United States Patent
Gagner et al.

(10) Patent No.: US 10,517,709 B2
(45) Date of Patent: Dec. 31, 2019

(54) METHODS AND DEVICES FOR ANCHORING A GASTROENTEROLOGIC SLEEVE

(75) Inventors: Michel Gagner, Montréal (CA); David J. Blaeser, Brooklyn Park, MN (US); Dale A. Spencer, Wayzata, MN (US)

(73) Assignee: Ballast Medical Inc., Montreal, Quebec (CA)

( * ) Notice: Subject to any disclaimer, the term of this patent is extended or adjusted under 35 U.S.C. 154(b) by 807 days.

(21) Appl. No.: 12/865,706

(22) PCT Filed: Jan. 30, 2009

(86) PCT No.: PCT/US2009/032737
§ 371 (c)(1),
(2), (4) Date: Dec. 15, 2010

(87) PCT Pub. No.: WO2009/097582
PCT Pub. Date: Aug. 6, 2009

(65) Prior Publication Data
US 2011/0098630 A1 Apr. 28, 2011

Related U.S. Application Data

(60) Provisional application No. 61/025,500, filed on Feb. 1, 2008.

(51) Int. Cl.
*A61F 2/04* (2013.01)
*A61B 17/00* (2006.01)
*A61F 5/00* (2006.01)

(52) U.S. Cl.
CPC ...... *A61F 2/04* (2013.01); *A61B 2017/00818* (2013.01); *A61F 5/0076* (2013.01); *A61F 2002/041* (2013.01); *A61F 2002/045* (2013.01)

(58) Field of Classification Search
CPC .. A61F 2/02; A61F 2/04; A61F 2/9511; A61F 2/958; A61F 2/962; A61F 2/9583; A61F 2002/044; A61F 5/003; A61F 5/0013–0033; A61F 5/0036–0046; A61F 5/0063–0073; A61F 5/0076–0079; A61F 5/0083–0086
USPC .............. 604/8, 9, 156–158, 171; 623/23.64–23.65, 23.67
See application file for complete search history.

(56) References Cited

U.S. PATENT DOCUMENTS

| 4,592,339 A | | 6/1986 | Kuzmak et al. | |
| 5,074,868 A | * | 12/1991 | Kuzmak | 606/157 |
| 5,431,640 A | * | 7/1995 | Gabriel | 604/270 |

(Continued)

FOREIGN PATENT DOCUMENTS

| WO | 2003086507 A1 | 10/2003 |
| WO | 2006102240 A2 | 9/2006 |

*Primary Examiner* — Tan-Uyen T Ho
*Assistant Examiner* — Ned T Heffner
(74) *Attorney, Agent, or Firm* — Inskeep IP Group, Inc.

(57) ABSTRACT

A gastroenterologic sleeve is anchored within the digestive tract, without tissue-puncturing mechanisms, by providing anchoring mechanisms that utilize the inherent shape of the stomach to prevent sleeve migration. In at least two embodiments, the anchoring mechanism expands to conform to the interior stomach walls. In other embodiments, internal pessary rings are held in place at the gastroesophageal junction by an external band. A delivery device is provided for implanting the various device transesophageally.

8 Claims, 5 Drawing Sheets

(56) References Cited

U.S. PATENT DOCUMENTS

| | | | |
|---|---|---|---|
| 5,820,584 A * | 10/1998 | Crabb | 604/500 |
| 6,666,848 B2 * | 12/2003 | Stone | 604/164.01 |
| 6,755,869 B2 | 6/2004 | Geitz | |
| 7,037,344 B2 * | 5/2006 | Kagan | A61F 2/04 606/151 |
| 7,314,489 B2 | 1/2008 | McKenna et al. | |
| 2003/0040804 A1 * | 2/2003 | Stack | A61F 2/04 623/23.7 |
| 2004/0092892 A1 * | 5/2004 | Kagan et al. | 604/264 |
| 2004/0092974 A1 * | 5/2004 | Gannoe et al. | 606/153 |
| 2005/0096673 A1 * | 5/2005 | Stack et al. | 606/151 |
| 2005/0096750 A1 * | 5/2005 | Kagan et al. | 623/23.65 |
| 2006/0064120 A1 | 3/2006 | Levine et al. | |

* cited by examiner

METHODS AND DEVICES FOR ANCHORING A GASTROENTEROLOGIC SLEEVE

CLAIM OF PRIORITY

This application is the U.S. National Phase of and claims priority to International Patent Application No. PCT/US2009/032737, International Filing Date Jan. 30, 2009, entitled Methods And Devices For Anchoring A Gastroenterologic Sleeve, which in turn claims priority to U.S. Provisional Patent Application Ser. No. 61/025,500, filed Feb. 1, 2008 by Gagner et al., entitled Methods And Devices For Anchoring A Gastroenterologic Sleeve, the contents of both of which are incorporated in their entireties herein.

BACKGROUND OF THE INVENTION

The present invention relates generally to improved methods and devices for anchoring a gastroenterologic sleeve within the stomach without reliance on sutures, staples, or other mechanisms that puncture the stomach wall. In addition to leaving the stomach walls free of punctures, the anchoring system of the present invention prevents movement of the sleeve in both directions, thereby preventing the sleeve from being passed through the digestive system but also from refluxing up the esophagus.

According to the Center for Disease Control (CDC), sixty six percent of American are overweight, and thirty two percent are obese, presenting an overwhelming health problem. From an economic standpoint, it is estimated that more than 100 billion dollars are spent on obesity and treating its major co-morbidities. This figure does not include psychological and social costs. Many health care experts consider obesity the largest health problem facing westernized societies and considered obesity an epidemic. From a medical standpoint, obesity is the primary risk factor for type 2 diabetes and obstructive sleep apnea. It increases the chances for heart disease, pulmonary disease, infertility, osteoarthritis, cholecystitis and several major cancers, including breast and colon cancers. Despite these alarming facts, treatment options for obesity remain limited.

Treatment options include dietary modification, very low-calorie liquid diets, pharmaceutical agents, counseling, exercise programs and surgery. Diet and exercise plans often fail because most individuals do not have the discipline to adhere to such plans. When diet and exercise fail, many try dietary supplements and drugs or other ingestible preparations promoted as being capable of suppressing appetite or inducing satiety. In general, these techniques for treating compulsive overeating/obesity have tended to produce only a temporary effect. The individual usually becomes discouraged and/or depressed after the initial rate of weight loss plateaus and further weight loss becomes harder to achieve. The individual then typically reverts to the previous behavior of compulsive overeating.

Surgical procedures that restrict the size of the stomach and/or bypass parts of the intestine are the only remedies that provide lasting weight loss for the majority of morbidly obese individuals. Surgical procedures for morbid obesity are becoming more common based on long-term successful weight loss result.

Bariatric surgery is a treatment for morbid obesity that involves alteration of a patient's digestive tract to encourage weight loss and to help maintain normal weight. Known bariatric surgery procedures include jejuno-ileal bypass, jejuno-colic shunt, biliopancreatic diversion, gastric bypass, Roux-en-Y gastric bypass, gastroplasty, gastric banding, vertical banded gastroplasty, and silastic ring gastroplasty. A more complete history of bariatric surgery can be found on the website of the American Society for Bariatric Surgery at http://www.asbs.orq, the contents of which are incorporated by reference herein in their entirety.

Most of the surgeries which create malabsorption, such as the by-pass operations, although effective in weight reduction, involve permanent modification of the GI tract and have a risk of short and long term complication and even death. By implanting a gastroenterologic sleeve, which is essentially a prosthetic liner for the stomach and/or duodenum, malabsorption can be induced without permanently modifying the GI tract. The sleeve simply provides a physical barrier between the food eaten and the absorptive stomach and duodenic walls.

Unfortunately, present gastroenterologic sleeve designs require fastening the sleeve to the tissue of the stomach or duodenum. Typically, this is accomplished through sutures, staples, or the like. Because the interior lining of the GI tract is incredibly slippery, it is very difficult to mechanically fasten anything to them. Additionally, anytime the walls of the GI tract are punctured, there is a risk of infection and other complications.

OBJECTS AND SUMMARY OF THE INVENTION

The methods and devices of the present invention are directed to methods and devices for implanting a gastroenterologic sleeve into the stomach and/or duodenum without using puncturing fasteners such as staples or sutures.

In one embodiment, a plurality of pessary rings is incorporated into a sleeve such that the rings expand until they contact the stomach walls. This embodiment takes advantage of the fact that the inlet and outlet of the stomach are much smaller than the interior of the stomach. Hence, once the rings have expanded, they are too large to migrate out of the stomach.

Another embodiment involves the use of a loose, yet expandable matrix implanted in the stomach. The matrix allows interaction between the stomach and food yet provides an anchor to which a sleeve lining the duodenum is attached. Hence, the matrix eliminates the possibility of the sleeve migrating through the intestinal tract.

Another embodiment employs two pessary rings and a band or other constrictor, such as a lap band. The pessary rings are installed inside the esophageal-stomach junction and have an inherent expansive force. A lap band is placed around the outside of the stomach, between the pessary rings, and has a squeezing force. Hence, the pessary rings and the lap band interact to lock each other in place. A sheath, tube or sleeve is attached to the pessary rings and extends into the stomach to cause food to bypass some or all of the stomach. The sheath may also extend into the duodenum such that a portion of the small intestine is also bypassed.

DETAILED DESCRIPTION OF THE INVENTION

Figure 1:
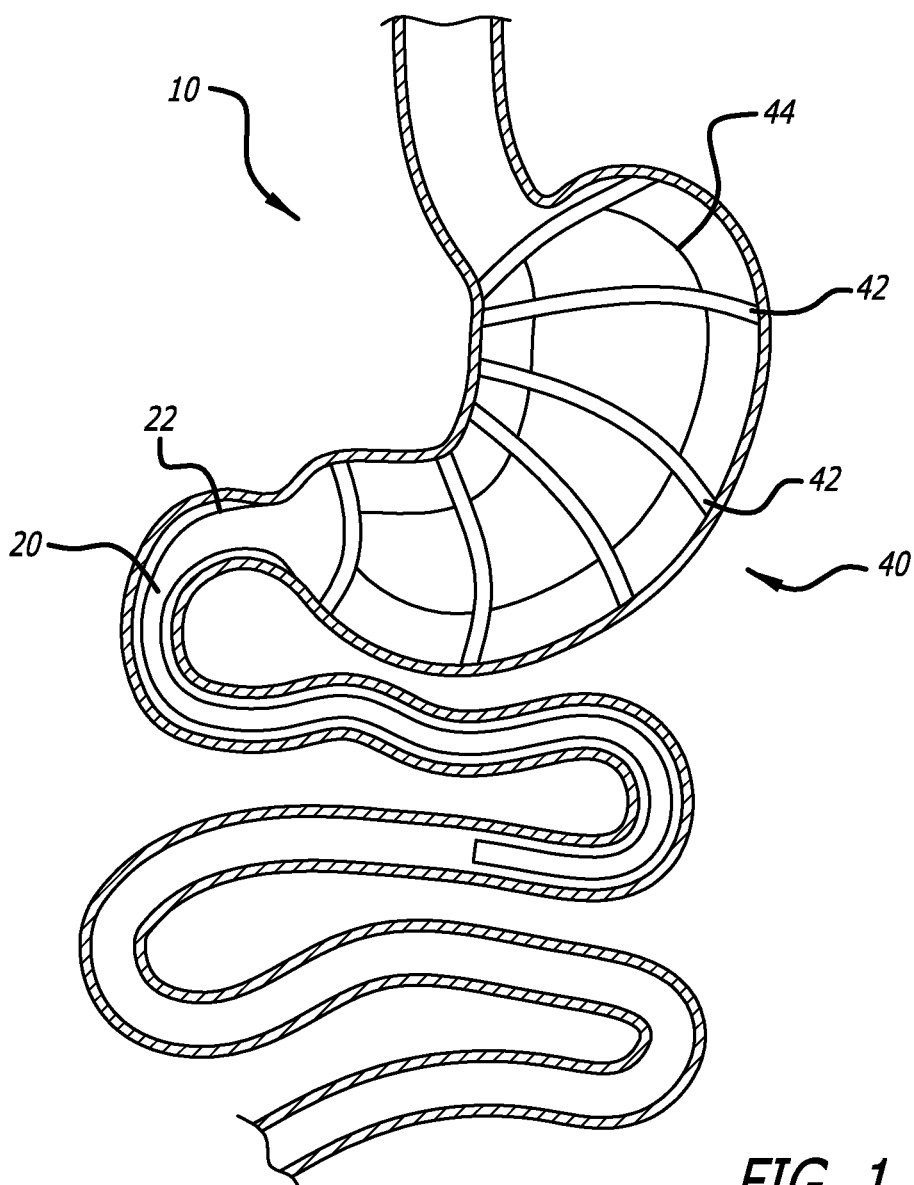
FIG. 1 is an elevation of an embodiment of the present invention installed within a stomach.

Referring now to the figures and first to FIG. 1 there is shown an embodiment of the present invention that includes a device 10 for creating a malabsorption condition in the stomach and/or duodenum. The device 10 generally includes an absorption-limiting or preventing sheath or tube 20 that is attached at a proximal end 22 to an anchoring device 40.

The anchoring device 40 includes a plurality of rings 42, such as pessary rings for example, connected together by thin connectors 44. The rings 42 are resilient and collapsible such that they may be compressed into elongate members for introduction into the stomach via the esophagus with a catheter or endoscope. Upon release from the delivery device, the rings 42 expand and orient themselves in a spaced-apart fashion. The rings are sized and arranged according to the shape of the stomach and it is envisioned that each device will be sized proportionately to the size of the patient, if necessary.

The connectors 44 are thin, thread-like connectors that prevent the rings 42 from twisting. The connectors 44 also function to combine the rings 42 into a single anchor and further create large gaps through which food may contact the stomach walls for digestion. In the event that it is desired to prevent the food from contacting the stomach walls, the thin connectors 44 may be replaced by a sleeve-like material. It is further envisioned that a combination of thin connectors 44 and connectors made of sleeve-like material may be used to control the area of the stomach that participates in the digestive process. It is further contemplated that the thin connectors 44 may be replaced by a semi-permeable sleeve material that allows some of the food to come into contact with stomach acid for digestion.

Figure 2:
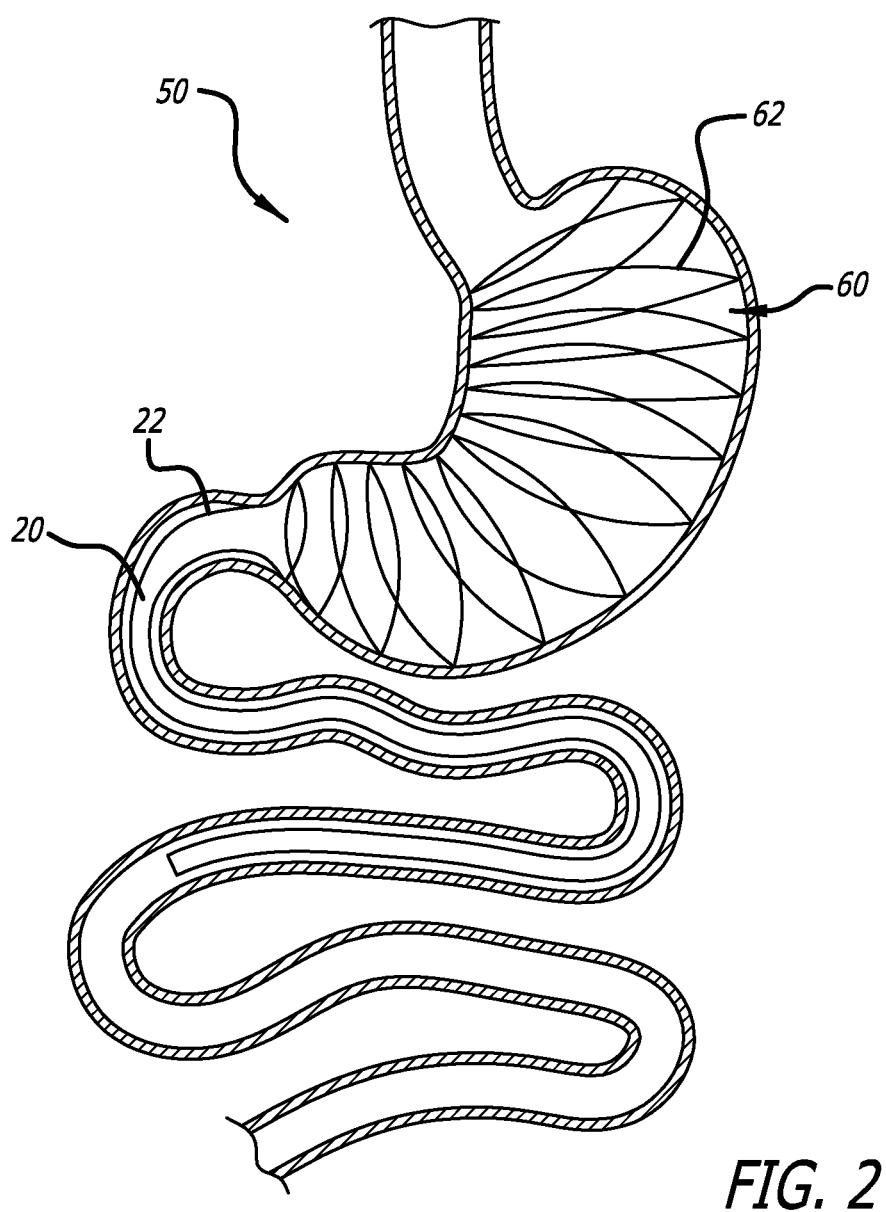
FIG. 2 is an elevation of an embodiment of the present invention installed within a stomach.

FIG. 2 shows another embodiment of a device 50 of the present invention. The device 50 also includes an absorption-limiting or preventing sheath or tube 20 that is attached at a proximal end 22 to an anchoring device 60. The anchoring device 60 is constructed of a loose, expandable matrix 62. The matrix 62 is constructed such that some or all of the food entering the stomach is permitted to interact with the stomach in the digestive process. The matrix may be constructed of a self-expanding material such as Nitinol, or any suitable, digestive-resistant material. The anchoring device 60 is sized to substantially fill the stomach cavity when expanded and also to conform to the shape of the stomach, thereby providing a stable anchor for the tube 20.

Figure 3:
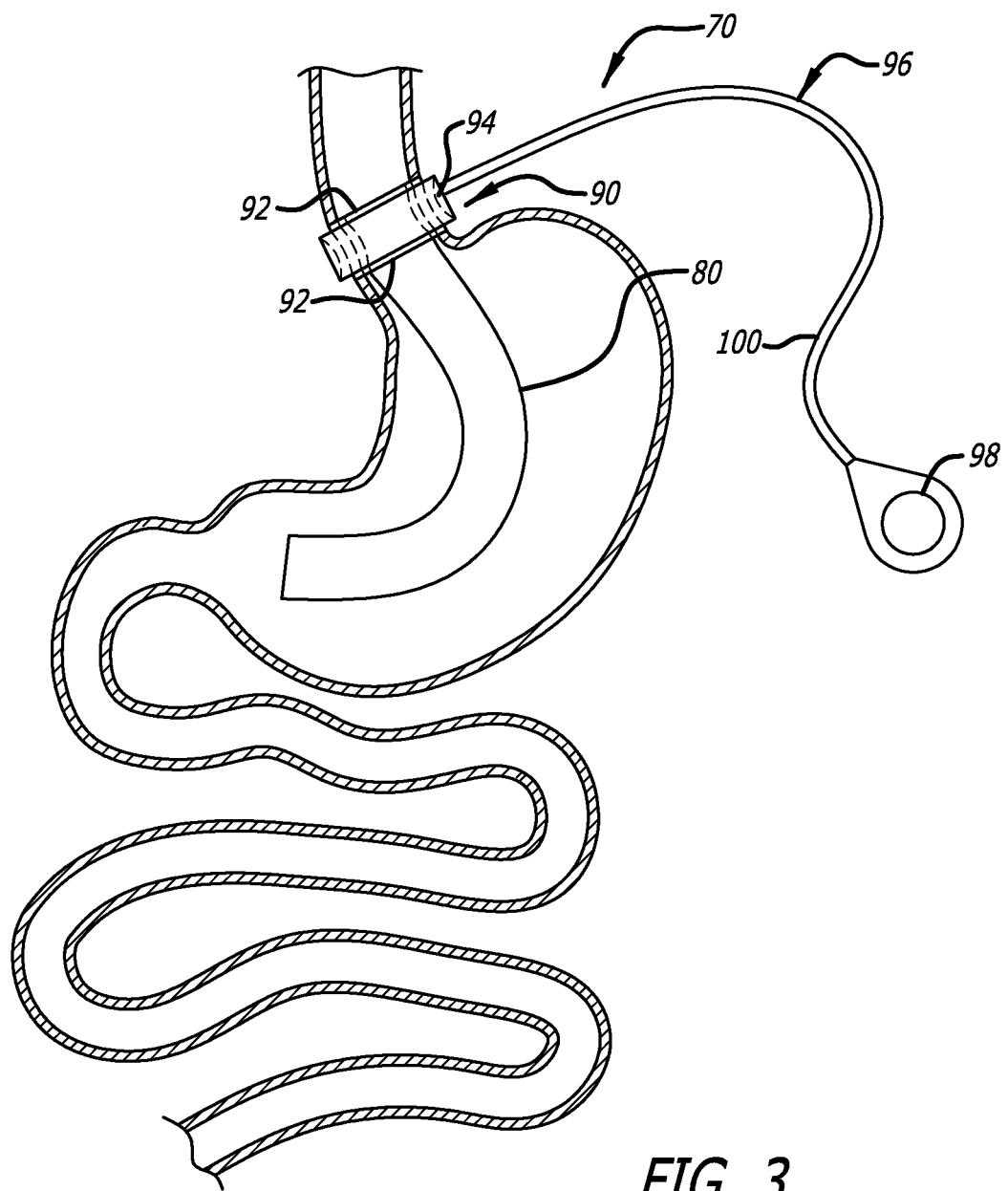
FIG. 3 is an elevation of an embodiment of the present invention installed within a stomach.

FIG. 3 shows an embodiment of a device 70 that includes sheath 80 connected to an anchoring device 90. The sheath 80 is sized and constructed to prevent food from contacting the upper stomach, thereby limiting digestion. At its upper end, the sheath 80 is connected to the anchoring device 90, which includes components that are internal and external to the gastroesophageal junction.

The interior components of the anchoring device 90 include two pessary rings 92, each connected to the sheath 80. The pessary rings 92 are self-expanding and, when in place, place a mild pressure on the inside of the esophagus.

The exterior components of the anchoring device 90 include a lap band 94 and an inflation device 96. The lap band 94 is fastened around the outside of the gastroesophageal junction between the locations of the pessary rings 92.

The anchoring device 90 also includes a pump 98, such as a hand pump, connected to the lap band 94 via a tube 100. Once the lap band 94 is fastened around the outside of the gastroesophageal junction between the locations of the pessary rings 92, the lap band 94 is inflated with an acceptable fluid, such that the lap band places an inward pressure on the gastroesophageal junction between the external pressure points of the pessary rings 92. In this way, the lap band 94 and the pessary rings 92 cooperate to prevent movement of the anchoring device 90. It is further contemplated that the lap band 94 can be controlled using the pump 98 to control the amount and rate that food can enter the stomach, as well as preventing gastroesophageal reflux disease (GERD).

Figure 4:
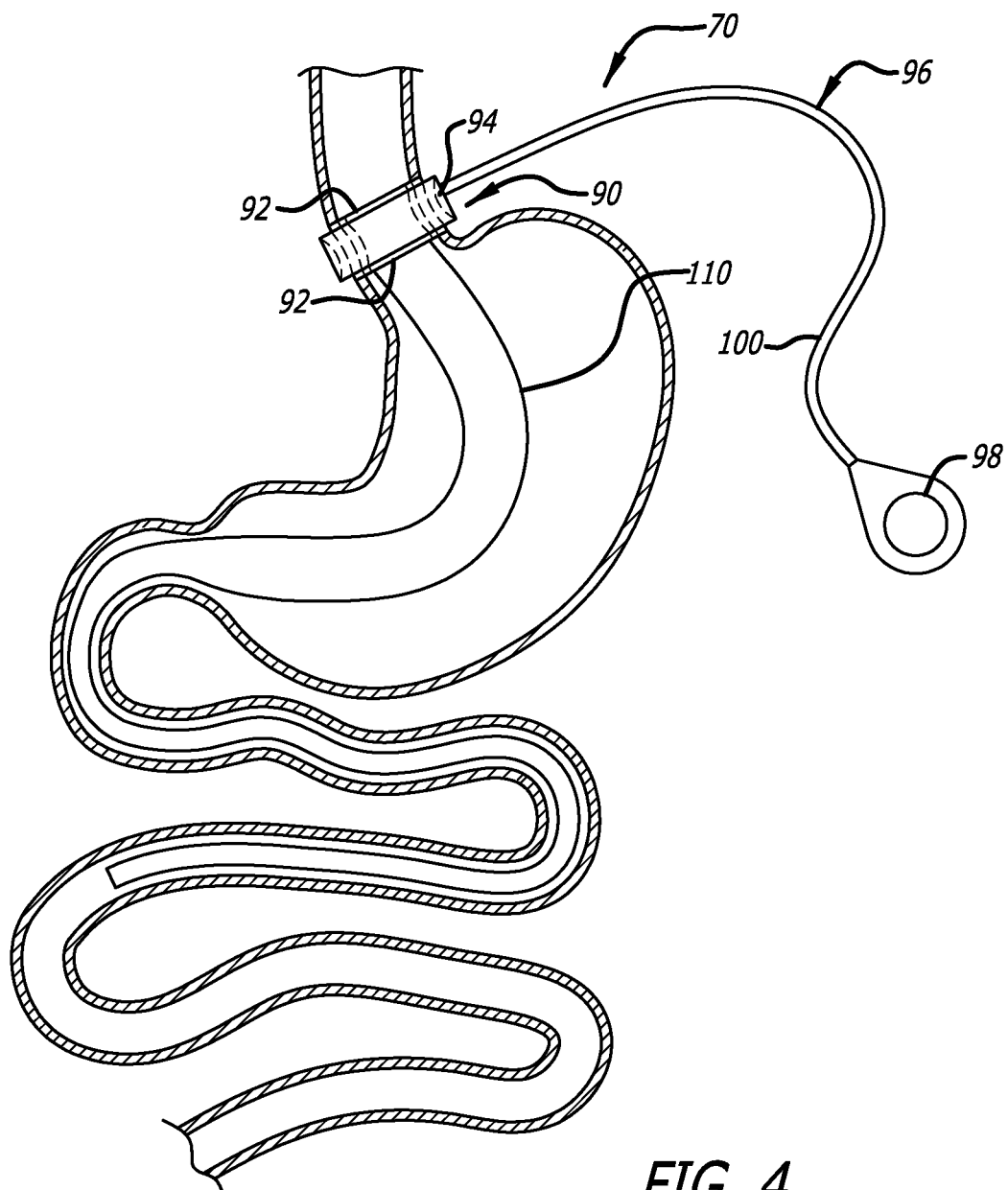
FIG. 4 is an elevation of an embodiment of the present invention installed within a stomach.

FIG. 4 depicts another embodiment of the device 70 in which a sheath 110 is attached to the anchoring device 90 is longer and extends well into the duodenum. This embodiment provides a solution for completely bypassing the stomach and some or all of the duodenum. However, it is envisioned that the sheath 110 could be constructed, partly or entirely, of a semi-permeable material that allows some gastric interaction between the food and the digestive system. Doing so may prevent some of the undesirable effects of malabsorption, such as the various forms of malabsorption syndrome.

Implantation

Figure 5:
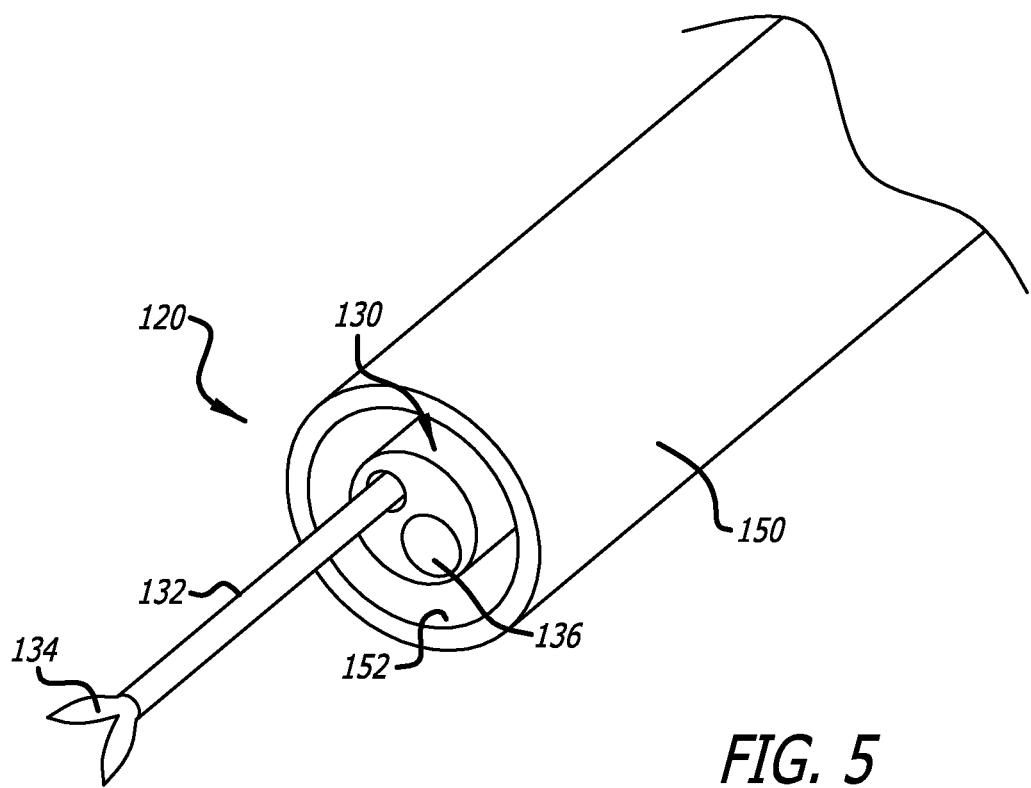
FIG. 5 is a perspective view of a delivery device that may be used to delivery the devices of the present invention.

The devices of FIGS. 1 and 2 may be implanted completely endoscopically, without the use of a general anesthesia. FIG. 5 shows one example of a delivery device 120 for use in implanting devices 10 or 50. The delivery device 120 includes a endoscopic catheter 130 surrounded by a sheath catheter 150. A space 152 exists between the endoscopic catheter 130 and the sheath catheter 150 that is sized to allow the device 10 or 50 to be tubularly loaded therein.

The endoscopic catheter 130 includes a pulling wire 132 with an attachment mechanism 134 at a distal end thereof. The endoscopic catheter 130 also includes an endoscope 136 and a steering device (not shown). Preferably, a portion of the endoscopic catheter 130, such as the pulling wire 132, is radiopaque. Alternatively, radiopaque bands may be incorporated into the distal end of the delivery device 120.

In operation, a device 10 or 50 is loaded into the delivery device 120 such that the endoscopic catheter 130 passes through the interior lumen of the device 10 or 50 and the sheath catheter 150 surrounds the exterior of the device 10 or 50. The device 10 or 50 is loaded such that the distal end of the device 10 or 50 is at the distal end of the delivery device 120. The attachment mechanism 134 is attached to the distal end of the device 10 or 50.

The delivery device 120 is then navigated transesophageally into and through the stomach and into the duodenum to a desired depth. The delivery device 120 is then retracted while the pulling wire 132 is advanced through the endoscopic catheter 130 such that the distal end of the pulling wire 132 remains somewhat stationary with respect to the duodenum. Hence, as the delivery device 120 is retracted, the pulling wire 132 pulls the device 10 or 50 from the distal end of the delivery device via the attachment mechanism 134.

As the delivery device 120 is retracted, the endoscope 136 provides an interior view of the device 10 or 50 being deployed. Hence, verification that the device 10 or 50 is not twisted or otherwise fouled is provided.

Once the delivery device 120 is retracted through the stomach, and the entire device 10 or 50 is deployed, the attachment device 134 is released from the distal end of the device 10 or 50 and the pulling wire 132 is retracted into the endoscopic catheter 130. Then the entire delivery device 120 is removed from the body.

The delivery device 120 may be similarly used to deploy the device 70 of FIGS. 3 and 4. However, laparoscopic installation of the lap band 94 is also required.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

We claim:

1. A device implantable in a digestive tract comprising a duodenum, a pylorus and a stomach having a fundus, a body and an antrum, the device comprising:
   an absorption-limiting sheath defined by a continuous tubular wall, the absorption-limiting sheath having a distal portion positionable within the duodenum and a proximal end sized and configured to terminate within the pylorus when the device is positioned in the digestive tract, the absorption-limiting sheath being configured to extend through the pyloric sphincter without exerting a radial pressure thereon; and
   an anchoring device capable of interacting with the digestive tract to prevent migration of the absorption-limiting sheath through the digestive tract without puncturing tissue of the digestive tract, the anchoring device comprising:
      a resilient ring attached to the proximal end of the absorption-limiting sheath, the resilient ring having an original size and being compressible to a compressed position for accommodation within an endoscope during delivery to the digestive tract, the resilient ring returning to the original size once positioned within the digestive tract.

2. The device of claim 1, wherein the anchoring device further comprises:
   at least one additional resilient ring; and
   a connecting mechanism connecting the resilient ring positionable in the pylorus and the at least one additional resilient ring to maintain the resilient ring positionable in the pylorus and the at least one additional resilient ring in a spaced-apart relationship; and
   wherein the absorption-limiting sheath is attached to a distalmost one of the resilient ring and the at least one additional resilient ring.

3. The device of claim 2, wherein the at least one additional resilient ring is positionable in the stomach and the connecting mechanism comprises a plurality of connector threads.

4. The device of claim 3, wherein the anchoring device is constructed and arranged to control an amount of the food entering the stomach that is permitted to interact with the stomach.

5. The device of claim 1, wherein the anchoring device further comprises:
   at least one additional resilient ring; and
   a sleeve attached to and extending between the resilient ring positioned in the pylorus and the at least one additional resilient ring.

6. The device of claim 5, wherein the sleeve is semipermeable.

7. A method of reducing interaction between food and a digestive tract comprising a duodenum, a pylorus and a stomach having a fundus, a body and an antrum, the method comprising:
   endoscopically inserting a device comprising an anchoring device and an absorption-limiting sheath defined by a continuous tubular wall into the digestive tract of a patient using an endoscopic catheter, the anchoring device comprising:
      a resilient ring positionable in the antrum in proximity of the pylorus, the resilient ring attached to a proximal end of the absorption-limiting sheath and having a respective original size and being compressible to a compressed position for accommodation within an endoscope;
   positioning a distal portion of the absorption-limiting sheath within the duodenum and the resilient ring in the pylorus such that the absorption-limiting sheath extends through the pyloric sphincter without exerting a radial pressure thereon and the proximal end of the absorption-limiting sheath terminates within the pylorus; and
   retracting the endoscopic catheter from the digestive tract to allow the resilient rings of the anchoring device to return to the respective original size once positioned in the pylorus without puncturing tissue of the digestive tract.

8. The method of claim 7, further comprising the step of directing the food through the device thereby preventing at least some of the food from contacting an area of the digestive tract.

* * * * *